United States Patent
Schäller et al.

(10) Patent No.: US 8,827,995 B2
(45) Date of Patent: Sep. 9, 2014

(54) SURGICAL INSTRUMENT FOR SEALING BLOOD VESSELS

(75) Inventors: Daniel Schäller, Tübingen (DE); Matthias Voigtländer, Gomaringen (DE); Klaus Fischer, Nagold (DE); Mara Szyrach, Zürich (DE); Lars Blobel, Ammerbuch-Entringen (DE); Irina Sigle, Mössingen (DE)

(73) Assignee: Erbe Elektromedizin GmbH, Tübingen (DE)

( * ) Notice: Subject to any disclaimer, the term of this patent is extended or adjusted under 35 U.S.C. 154(b) by 1063 days.

(21) Appl. No.: 12/741,396

(22) PCT Filed: Nov. 4, 2008

(86) PCT No.: PCT/EP2008/009289
§ 371 (c)(1),
(2), (4) Date: Jun. 28, 2010

(87) PCT Pub. No.: WO2009/059741
PCT Pub. Date: May 14, 2009

(65) Prior Publication Data
US 2010/0262141 A1    Oct. 14, 2010

(30) Foreign Application Priority Data

Nov. 5, 2007 (DE) .................... 10 2007 052 641
Dec. 27, 2007 (DE) .................... 10 2007 062 786

(51) Int. Cl.
*A61B 18/14* (2006.01)
*A61B 17/12* (2006.01)
*A61B 17/285* (2006.01)
*A61B 17/00* (2006.01)
*A61B 18/00* (2006.01)
*A61B 17/32* (2006.01)
*A61B 19/00* (2006.01)

(52) U.S. Cl.
CPC ..... *A61B 18/1442* (2013.01); *A61B 2018/1412* (2013.01); *A61B 2018/1455* (2013.01); *A61B 17/285* (2013.01); *A61B 17/12022* (2013.01); *A61B 2017/00084* (2013.01); *A61B 17/12195* (2013.01); *A61B 2018/00404* (2013.01); *A61B 2017/320052* (2013.01); *A61B 17/12186* (2013.01); *A61B 17/12109* (2013.01); *A61B 2017/00504* (2013.01); *A61B 2019/463* (2013.01); *A61B 2017/00022* (2013.01); *A61B 17/00491* (2013.01); *A61B 2017/005* (2013.01); *A61B 2018/00601* (2013.01)
USPC ................ 606/51; 606/52; 606/214

(58) Field of Classification Search
USPC ................ 606/49, 51, 52, 213–216
See application file for complete search history.

(56) References Cited

U.S. PATENT DOCUMENTS 5,336,221 A * 8/1994 Anderson .................. 606/27
5,383,899 A * 1/1995 Hammerslag ............. 606/214
(Continued)

FOREIGN PATENT DOCUMENTS

DE    42 42 143 C2    6/1994
DE    44 29 647 C2    2/1996
(Continued)

OTHER PUBLICATIONS

International Preliminary Report on Patentability and Written Opinion (English Translations) for PCT/EP2008/009289.

*Primary Examiner* — Linda Dvorak
*Assistant Examiner* — Jocelyn D Ram
(74) *Attorney, Agent, or Firm* — Dickstein Shapiro LLP

(57) ABSTRACT

A surgical instrument including an injection device and a dosing device. These devices are designed such that a predetermined amount of an adhesive or an adhesive containing filler can be injected into a sealing section of the blood vessel. The blood vessel can then be cut at the filled point and is sealed on both sides.

13 Claims, 6 Drawing Sheets

(56) References Cited

U.S. PATENT DOCUMENTS

| | | | |
|---|---|---|---|
| 5,725,568 A | 3/1998 | Hastings | |
| 6,033,427 A | 3/2000 | Lee | |
| 6,391,048 B1 * | 5/2002 | Ginn et al. | 606/213 |
| 6,723,092 B2 * | 4/2004 | Brown et al. | 606/41 |
| 7,571,845 B2 * | 8/2009 | Viola | 227/180.1 |
| 7,625,370 B2 * | 12/2009 | Hart et al. | 606/27 |
| 2001/0016750 A1 | 8/2001 | Malecki et al. | |
| 2002/0099372 A1 | 7/2002 | Schulze et al. | |
| 2002/0165541 A1 * | 11/2002 | Whitman | 606/48 |
| 2002/0165593 A1 | 11/2002 | Hayashi et al. | |
| 2003/0097149 A1 * | 5/2003 | Edwards et al. | 606/214 |
| 2005/0165444 A1 * | 7/2005 | Hart et al. | 606/213 |
| 2006/0025816 A1 * | 2/2006 | Shelton | 606/215 |
| 2006/0167452 A1 | 7/2006 | Moses et al. | |
| 2010/0049194 A1 * | 2/2010 | Hart et al. | 606/51 |
| 2011/0098700 A1 * | 4/2011 | Tamai et al. | 606/41 |

FOREIGN PATENT DOCUMENTS

| | | |
|---|---|---|
| EP | 0 997 108 A2 | 5/2000 |
| JP | 4-33653 A | 2/1992 |
| JP | 2008-505697 A | 2/2008 |
| WO | WO 2005/082299 A2 | 9/2005 |
| WO | WO 2006/017023 A2 | 2/2006 |
| WO | WO 2007/058877 A2 | 5/2007 |

* cited by examiner

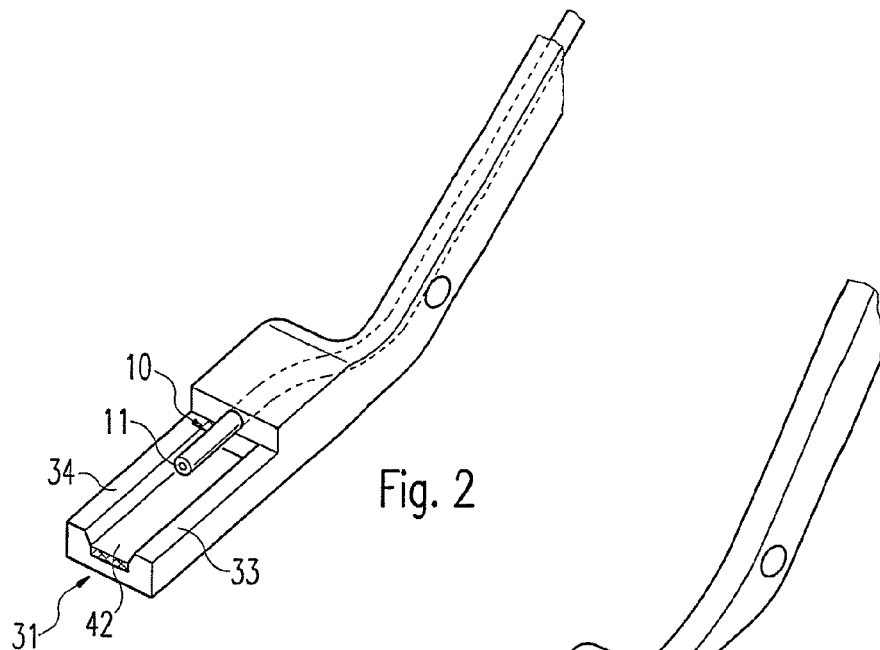
Fig. 2
Fig. 3
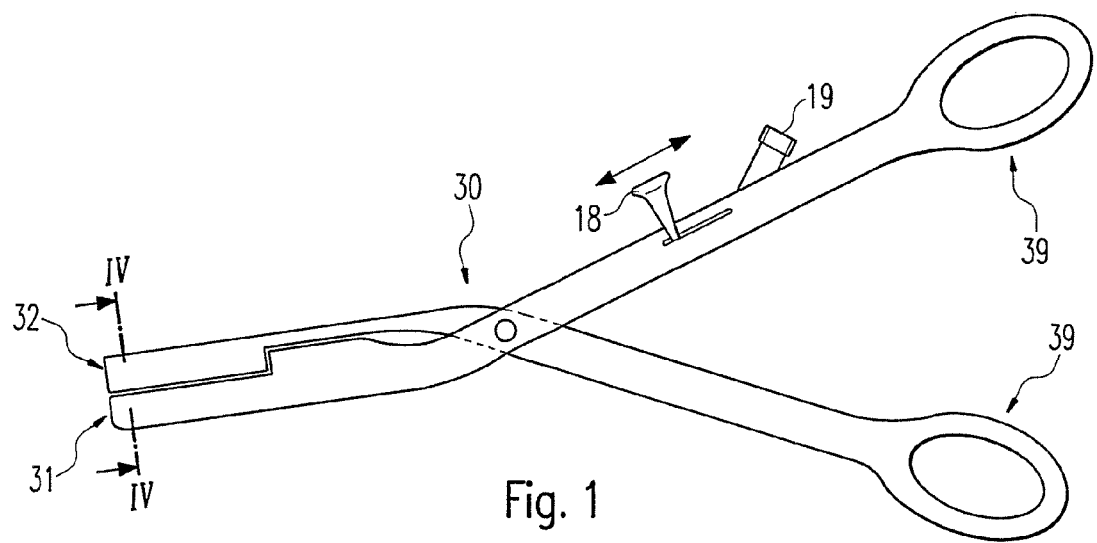
Fig. 1

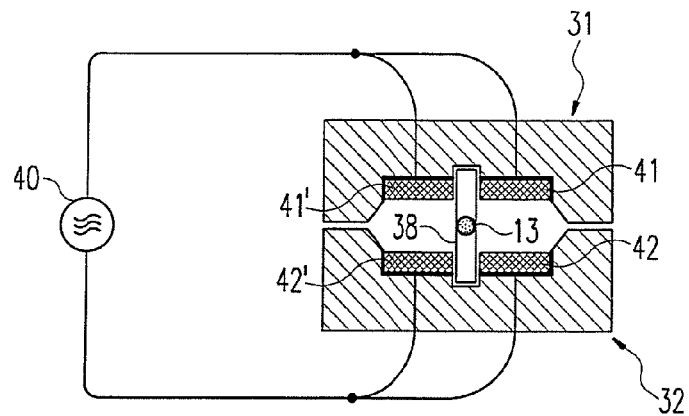
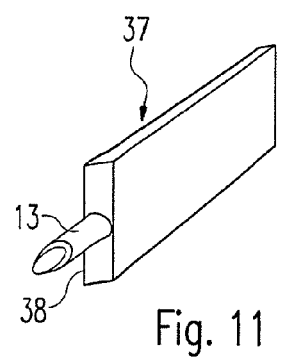
Fig. 10
Fig. 11
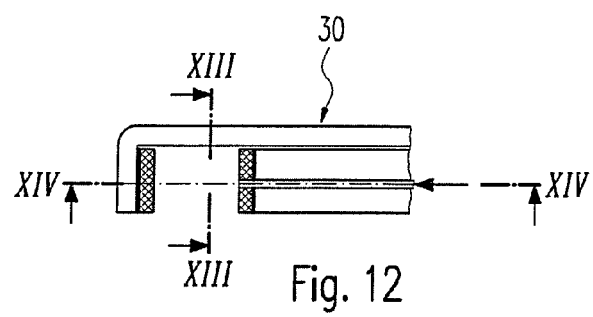
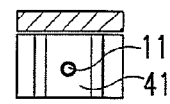
Fig. 12
Fig. 13
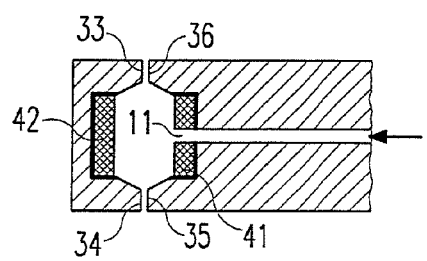
Fig. 14

SURGICAL INSTRUMENT FOR SEALING BLOOD VESSELS

FIELD OF THE DISCLOSED EMBODIMENTS

The disclosed embodiments relate to a surgical instrument for sealing blood vessels and a heat-curable adhesive as a medicament.

BACKGROUND

During surgery, blood vessels often have to be severed and sealed after severing to prevent bleeding. Such sealing of blood vessels is normally carried out with a "thread ligature" in which both ends of the vessel are ligated with a thread before the blood vessel is severed therebetween.

In the case of more recent methods, a high-frequency coagulation is carried out with surgical pincers or forceps, in the case of which a minimum contact force is exerted on the vessel walls with two mutually opposite surface electrodes, while the high-frequency (HF) energy input via the surface electrodes ensures heating of the vessel material. Coagulation and a bonding of the mutually opposite vessel walls are thus brought about, with the vessel being "sealed." Such coagulation instruments are known, for example, from DE 42 42 143 C2 or EP 0 997 108 A2.

While smaller vessels (under 1 mm diameter) are sealed by their inherent contraction process, the sealing of larger vessels is problematic since the sealing points must also be able to withstand the maximum internal vessel pressure of the circulatory system. This problem increases with the size (the diameter) of the blood vessel.

SUMMARY

It is an object of the disclosed embodiments to provide a device (and a medicament) for achieving a simple and reliable sealing of blood vessels.

According to disclosed embodiments, in order to seal a blood vessel, an adhesive is injected into the blood vessel so that the blood vessel can be severed after curing of the adhesive. Complicated handling of the adhesive is thus not required.

The term "adhesive" refers very generally in this case to an active ingredient which is suitable for connecting the surfaces to one another. This can therefore equally be an adhesive in the technical sense, such as for example, an active ingredient which brings about this connection via an enzymatic reaction (i.e., indirectly).

To be more precise, the disclosed embodiments include a surgical instrument for sealing blood vessels which includes an injection device and a dosing device. These devices are designed such that a predetermined amount of an adhesive or of an adhesive (or active ingredient) containing filler can be injected into a sealing section of the blood vessel.

Additionally, according to disclosed embodiments, only a defined sealing section of the blood vessel is filled with adhesive. In other words, the adhesive does not migrate further in the blood vessel.

A clamp device may also be provided which has gripping elements formed such that the blood vessel can be gripped and sealed at sealing points spaced apart from one another such that the sealing section of the blood vessel which can be filled with the adhesive remains between the sealing points. As a result, a further migration of the adhesive into the blood vessel is prevented in a simple manner.

The injection device is preferably connected to the clamp device such that the adhesive can be injected into the sealing section. The clamp device and the injection device are therefore defined in their spatial positions with respect to one another so that visually controlled targeting and complicated handling are superfluous.

The injection device preferably has a nozzle which is movable and includes a pressure-generating device formed such that the adhesive can be injected into the blood vessel while forming a sufficiently powerful jet. In this case, an injection needle is therefore not used, which leads to the design of the surgical instrument being very simple.

Alternatively, the injection device can include a movable needle and a pressure-generating device which is formed such that the adhesive can be injected into the blood vessel by means of the needle. Particularly in the case of this embodiment, single-use cartridges, comprising the injection needle, a plunger and a cylinder located therein, can be used, which reliably prevents sterility problems. Herein, the injection device can be formed such that the needle can be moved, in particular hydraulically, by the pressure-generating device. In this case, no further mechanical parts are therefore required.

An energy-supply device for heating up and/or coagulating the sealing section is may also be provided. If the sealing section or the vessel sections located there are coagulated, a particularly robust sealing is achieved. Moreover, the adhesive may be cured, by heating or another form of energy supply, if a corresponding adhesive, which acts in this case as a medicament, is used. Particularly if the adhesive is additionally provided with fillers, a large cross-section of a vessel can also be sealed in a simple manner.

The energy-supply device preferably comprises electrodes between the gripping elements for passing a high-frequency current through the blood vessel and indeed restricted to the sealing section. This is known per se for the purpose of coagulation. If the adhesive is electrically conductive and/or is provided with electrically conductive fillers, in this manner heating can be brought about with particular ease for curing of the adhesive.

A cutting device may also be provided for severing the blood vessel in the region of the sealing section. Severing of the vessel can be carried out in this manner with one and the same surgical instrument in a time-saving manner.

A measurement device for determining a filling state of the sealing section may also be provided. As a result, it is possible to control precisely the amount of adhesive which is injected into the sealing section. This measurement device is preferably connected to the injection device via a first control unit for control of an injection time and/or an injection profile and/or an injection amount. Control of the filling procedure which is only possible for experienced surgeons is thus superfluous.

An additional measurement device for determining a temperature and/or coagulation state of the sealing section may also be provided so that complete control of the operation procedure is possible. This measurement device is preferably connected via a second control unit to an energy-supply device for the supply of energy to the sealing section in order to control the amount of energy so that in this case surgeons with relatively little experience are able to use the surgical instrument.

The measurement devices may be formed as impedance measurement devices for measuring an electric impedance of the blood vessel, particularly in the region of the sealing section.

This measurement parameter reproduces precise measurement data which makes it possible to monitor the operation procedure in a relatively simple manner. While simultaneously using the electrodes provided for coagulating and/or heating the sealing section, this impedance measurement device is preferably combined so that the electrodes can be used both as coagulation electrodes and measurement electrodes. In this case, switching is preferably carried out between the energy source (high-frequency generator) and the measurement device (impedance measurement device) in relatively short time intervals so that the profile of the coagulation or heating procedure can be precisely determined.

The disclosed embodiments also relate to a heat-curable adhesive as a medicament which can be used in the described manner. In particular, this medicament is outstandingly suitable for sealing blood vessels and preferably comprises a filler or a filler mixture so that even larger cross-sections of vessels can be reliably sealed.

The adhesive may have an elevated conductivity such that it can be heated by passing through an electric current, in particular a high-frequency current, to allow curing in a controlled and simple manner. Herein, curing temperatures are particularly preferred which lie above normal room temperature or also body temperature, therefore preferably above 38° C., more preferably above 42° C. and particularly preferably above 55° C., therefore at temperatures in which tissue begins to coagulate. In this manner, it is ensured that the adhesive only cures where it is supposed to cure, namely in the sealing section. The adhesive is biocompatible and preferably formed in such a manner that breakdown of uncured adhesive components can take place in the body.

BRIEF DESCRIPTION OF THE DRAWINGS

Preferred embodiments are explained in greater detail below with reference to the illustrations.

FIG. 1 illustrates a side view of a surgical instrument or device of a disclosed embodiment.

FIGS. 2 and 3 are perspective views of the end sections of the device according to FIG. 1.

FIG. 10 is a cross-sectional view similar to that according to FIG. 4, but of another disclosed embodiment.

FIG. 11 is a perspective partial view of a cutting device according to a disclosed embodiment.

FIG. 12 is a side view of a surgical instrument or device in accordance with another disclosed embodiment.

FIG. 13 is a cross-sectional view along line XIII-XIII from FIG. 12.

FIG. 14 is a cross-sectional view along line XIV-XIV from FIG. 12.

DETAILED DESCRIPTION

Figure 4:
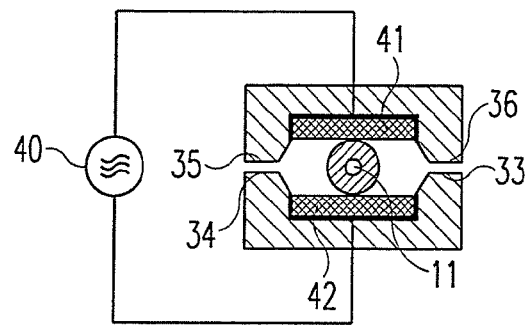
FIG. 4 is a cross-sectional along line IV-IV from FIG. 1.

In the following description, the same reference numbers are used for identical and identically acting parts.

FIG. 1 shows a top view of a scissors-like embodiment of the clamp device 30 according to a disclosed embodiment. This clamp device 30 includes grip sections 39 which are connected to one another via a joint. Gripping sections 31, 32, with which a vessel can be gripped, are provided opposite the grip sections 39 with respect to the joint. An actuating lever 18 for actuating an injection device (described further below) is provided on a branch of grip sections 39. A fluid-supply device 19 is also provided on a branch of grip sections 39.

FIGS. 2 and 3 show perspective top views of gripping sections 31 and 32. As can be seen in the drawings, gripping sections 31, 32 are trough-shaped and each include case gripping elements 33, 34 or 35, 36 and, between these, deeper lying electrodes 41 or 42 which are fitted so that they are insulated from gripping elements 33-36. Electrodes 41, 42 can be connected via electric connection elements (not shown) to a high-frequency generator.

Gripping section 31 also includes an injection device 10 with a nozzle 11, whose function is explained below. Herein, nozzle 11 is positioned symmetrically (as shown in FIG. 4) such that it sits centrally between both electrodes 41, 42.

Figure 5:
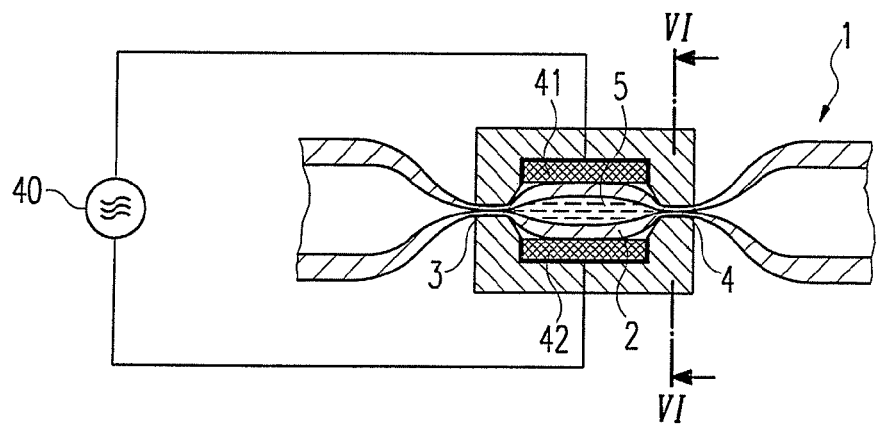
FIG. 5 is a view of the arrangement according to FIG. 4, but with a "clamped" vessel.
Figure 6:
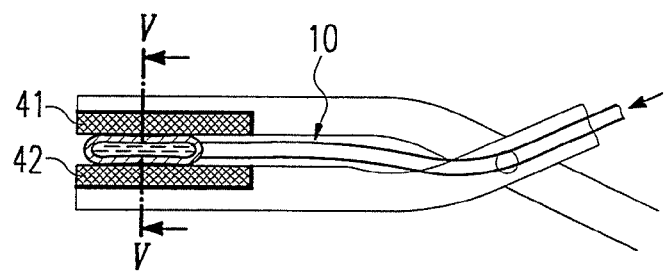
FIG. 6 is a cross-sectional along line VI-VI from FIG. 5.

If a vessel 1 is gripped with clamp device 30, as shown in FIGS. 5 and 6 (in two different sectional planes), the vessel walls are pressed together by gripping elements 33-36 so that sealing points 3, 4 are formed at which vessel 1 is sealed in an entirely impervious manner. A cavity, in which a sealing section 2 of vessel 1 is formed which is delimited on both sides by sealing points 3, 4, is formed between sealing points 3, 4 as a result of the fact that gripping sections 31, 32 are trough-shaped. In other words, electrodes 41, 42 which form the respective trough base are set back with respect to gripping elements 33-36.

As shown in FIG. 5, an adhesive (which may also include a filler and fills sealing section 2 after the injection) is injected into this sealing section 2 by means of nozzle 11. In the embodiment shown, the injection of the adhesive is carried out via an elevated pressure (similar to devices known from water-jet surgery), to which end injection device 10, as shown in FIG. 6, is placed with its nozzle 11 directly on the outer wall of blood vessel 1 in the region of sealing section 2.

The adhesive preferably cures directly in the case of an elevated temperature or by a passing through of electric current. Blood vessel 1 is furthermore coagulated, i.e. devitalised, in the region of sealing section 2, if this is desired, by passing a high-frequency current through the vessel 1. This is indicated in high-frequency generators 40 shown in FIGS. 4 and 5.

As soon as the adhesive 5 has cured, it forms a stopper connected in an adhesive manner to the walls of blood vessel 1. This stopper can now be cut so that blood vessel 1 is reliably sealed.

Figure 7:
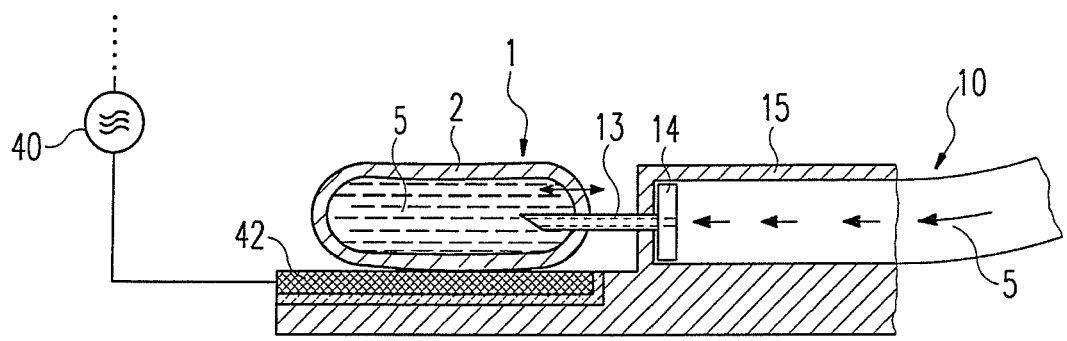
FIG. 7 illustrates a partial view of an injection device according to a disclosed embodiment.
Figure 8:
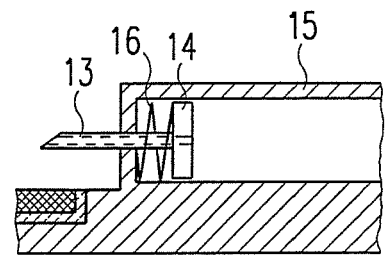
FIG. 8 is a detailed representation of a portion of the injection device according to FIG. 7.

In the variant shown in FIG. 7, adhesive 5 is injected into sealing section 2 by means of an injection needle 13. The tip at the opposite end of the injection needle 13 sits in a plunger 14 which is in turn movable in a cylinder 15. In the idle state, the injection needle 13 occupies a retracted position so that its tip does not project out of cylinder 15. This can—as shown in FIG. 8—be brought about by a restoring spring 16. In the embodiments shown in FIGS. 7 and 8, the injection needle 13 is also moved by the injection of the adhesive 5 itself.

Figure 9:
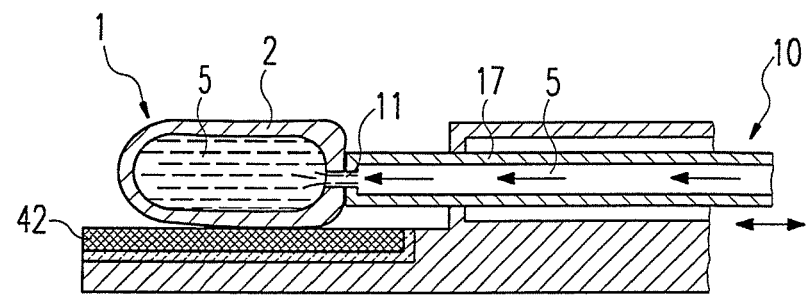
FIG. 9 illustrates a partial view of an injection device according to another disclosed embodiment, in a view similar to that according to FIG. 7.

In the embodiment shown in FIG. 9, the injection is brought about by an elevated pressure (similar to water-jet surgery). In this embodiment, tube 17, in which nozzle 11 sits, is also moved and placed on blood vessel 1 or sealing section 2 for injection of the adhesive 5.

In the embodiment shown in FIGS. 7 and 11, a cutting device 37 is additionally provided. At the front end thereof, there is a cutting edge 38 which can cut through blood vessel 1 in the region of sealing section 2 after curing of the adhesive 5. Injection needle 13 is further fitted in cutting device 37 so that an extremely compact design is produced.

In this embodiment, the electrodes are divided into subsections 41, 41' or 42, 42' so that cutting device 37 runs in a guided fashion in gripping sections 31, 32. In this embodiment, instead of a needle 13, the device may operate with a nozzle 11 through which adhesive is injected into blood vessel 1 with elevated pressure.

The embodiment according to FIGS. 12-14 shows the distal section of a clamp device 30 formed in a different manner in which there are not two branches connected via a joint, but rather a slidingly movable arrangement is made. In this arrangement, nozzle 11 sits directly in the surface of one electrode 41. A needle 13 may also be used in this embodiment.

In the case of the embodiments shown above, in particular in the embodiment according to FIGS. 7-9, injection devices 10 are provided which are connected via a tube to a corresponding pump device. It is, however, also possible in all cases to provide single-use containers in which an at least sufficient amount of adhesive is stored. These single-use containers can be provided either with a needle 13 or a corresponding nozzle 11, which makes it easy to satisfy sterility requirements.

Figure 15:
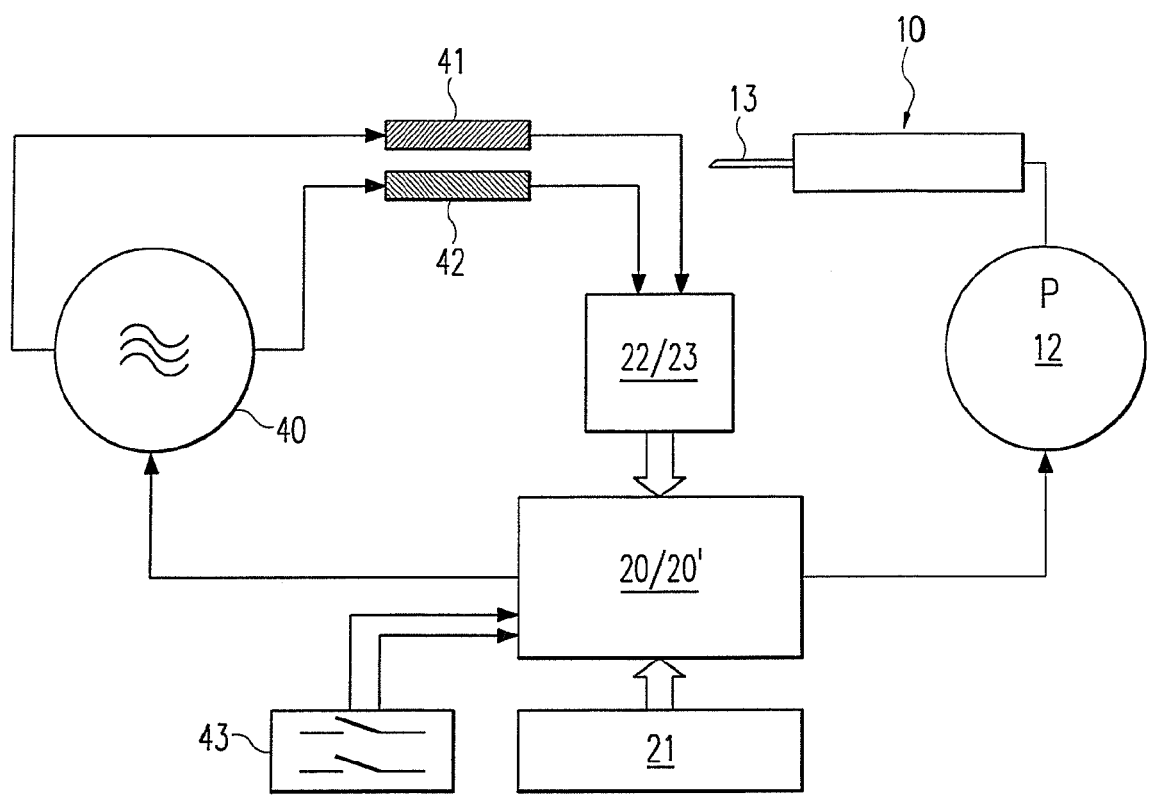
FIG. 15 is a schematic of the overall design of the surgical instrument with peripheral devices in accordance with a disclosed embodiment.

FIG. 15 shows in a schematic form an overall design which serves for the use of the surgical instrument according to the invention.

The electrodes 41, 42 and are connected to generator 40 which is controlled by a control device 20, 20'. Electrodes 41, 42 are further connected to a measurement device 22, 23 which is formed such that the impedance between electrodes 41, 42, i.e. the impedance of sealing section 2, can be measured. The measurement values are supplied to control unit 20, 20'.

Control unit 20, 20' also controls a pressure-generating device 12, which feeds injection device 10, so that fluid can be injected into sealing section 2 via needle 13 shown here.

An adjustment device 21 for adjusting the various parameters of generator 40 and pressure-generating device 12 as well as a switching device 43, which can be a foot or finger switch, are furthermore provided to influence control unit 20, 20'. The mode of operation of the individual parts has already been described further above.

Figure 16:
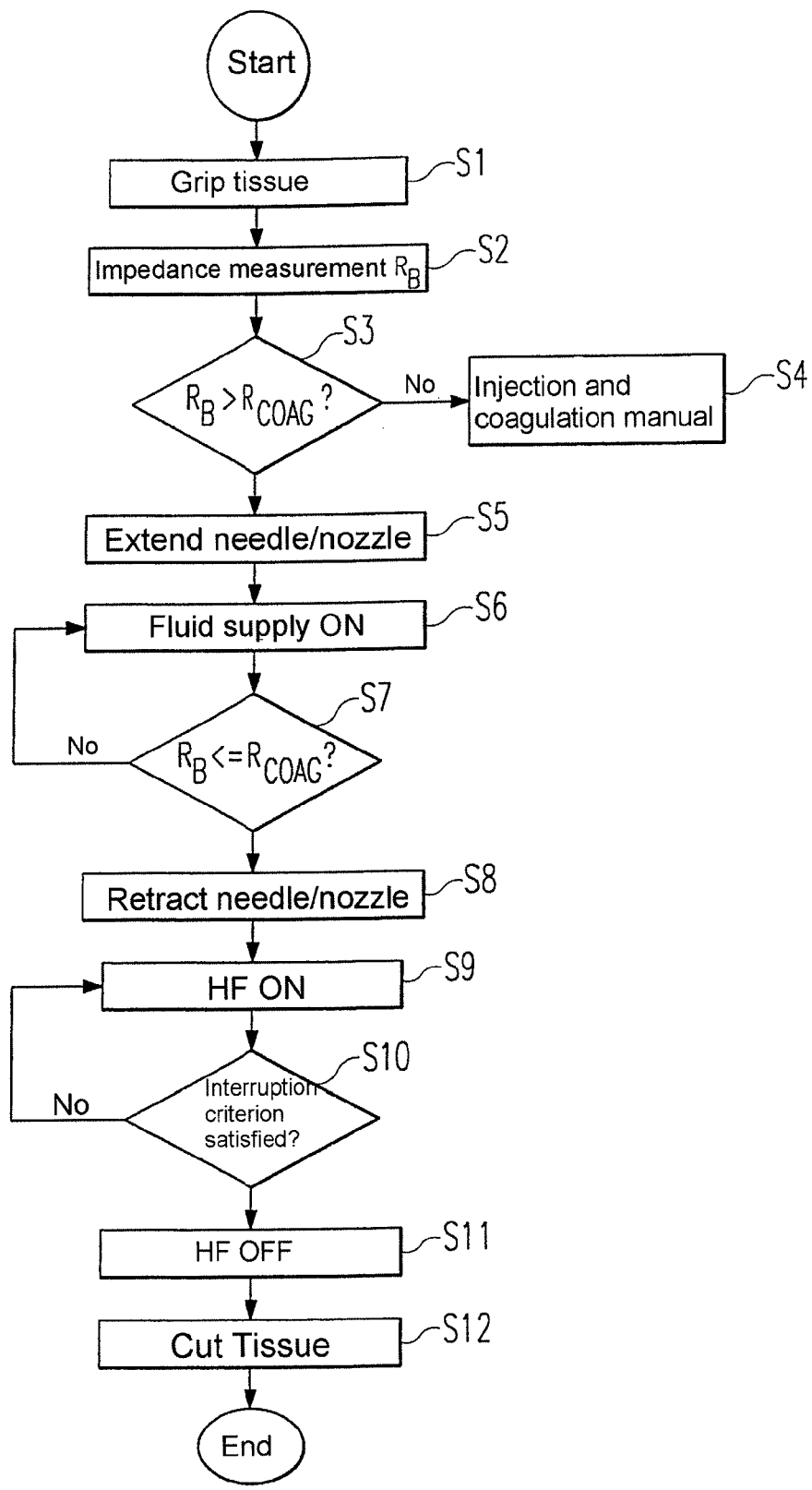
FIG. 16 is a flow chart illustrating the operation of the surgical instrument in accordance with disclosed embodiments.

FIG. 16 shows a schematic (simplified) flow chart.

In a first step S1, the tissue is gripped (by the surgeon). This is followed by step S2 in which an impedance measurement in which measurement device 22/23 measures the impedance between electrodes 41, 42.

In step S3, a query is made as to whether impedance $R_B$ is greater than a predetermined impedance $R_{COAG}$, i.e. an impedance which indicates that the tissue wall has sufficient contact to the active electrode. If this is not the case, in step S4 a manual injection and coagulation can take place and the automatism is stopped.

Otherwise, in step S5, the needle or the nozzle is extended so that the needle penetrates into the vessel or the nozzle adjoins the vessel.

In step S6, the fluid supply is activated, i.e. adhesive including filler is therefore injected.

In step S7, a query is made as to whether resistance $R_B$ is less than or equal to predetermined impedance $R_{COAG}$. If this is not the case, step S6 is repeated, i.e. further fluid is injected.

If, however, this is the case, in step S8, the needle or the nozzle is retracted and the high-frequency current is activated, in step S9.

In step S10, an interruption criterion is tested, on the basis of which it is decided whether the tissue is sufficiently coagulated and/or the adhesive is sufficiently cured. If this is not the case, step S9 is repeated.

If this is not the case, in step S11, the energy supply is deactivated (by the high-frequency source or another energy source).

Thereafter, in step S12, the tissue is severed. Both ends of the vessel are thus correctly sealed.

It should be pointed out here that all the above described parts and in particular the details illustrated in the drawings are essential for the disclosed embodiments alone and in combination. Adaptations thereof are the common practice of persons skilled in the art.

The invention claimed is:

1. A surgical instrument for sealing a blood vessel, the instrument comprising:
    an injection device for injecting an adhesive into the blood vessel;
    a dosing device, the injection device and dosing device being configured such that a predetermined amount of the adhesive can be injected into a sealing section of the blood vessel;
    a clamp device comprising gripping elements, wherein the gripping elements are formed trough-shaped such that the blood vessel can be gripped and sealed at sealing points spaced apart from one another such that the sealing section of the blood vessel which can be filled with the adhesive remains between the sealing points; and
    an energy-supply device for heating up and/or coagulating the sealing section, the energy-supply device further comprising electrodes between the gripping elements, which form the respective trough base of the trough-shaped gripping elements, for passing a high-frequency current through the blood vessel, restricted to the sealing section.

2. The surgical instrument according to claim 1, wherein the adhesive further comprises a filler.

3. The surgical instrument according to claim 1, wherein the injection device is connected to the clamp device such that the adhesive can be injected into the sealing section.

4. The surgical instrument according to claim 1, wherein the injection device comprises a nozzle and a pressure-generating device which are formed such that the adhesive can be injected into the blood vessel while forming a sufficiently powerful jet.

5. The surgical instrument according to claim 1, wherein the injection device comprises a needle and a pressure-generating device which are formed such that the adhesive can be injected into the blood vessel by means of the needle.

6. The surgical instrument according to claim 5, wherein the injection device is formed such that the needle can be moved hydraulically by the pressure-generating device.

7. The surgical instrument according to claim 1, further comprising a cutting device for severing the blood vessel in the region of the sealing section.

8. The surgical instrument according to claim 1, further comprising a measurement device for determining a filling state of the sealing section.

9. The surgical instrument according to claim 8, wherein the measurement device is connected to the injection device via a control unit for control of an injection time and/or injection profile and/or injection amount.

10. The surgical instrument according to claim 8, wherein the measurement device is formed as an impedance measurement device for measuring an electric impedance of the blood vessel in the region of the sealing section.

11. The surgical instrument according to claim 1, further comprising a measurement device for determining a temperature and/or coagulation state of the sealing section.

12. The surgical instrument according to claim 11, wherein the measurement device is connected via a control unit to the energy-supply device for the supply of energy to the sealing section in order to control an amount of energy.

13. The surgical instrument according to claim 11, wherein the measurement device is formed as an impedance measurement device for measuring an electric impedance of the blood vessel in the region of the sealing section.

* * * * *